(12) United States Patent
Johnson (10) Patent No.: US 11,020,198 B2
(45) Date of Patent: Jun. 1, 2021

(54) SLACK CABLE ELIMINATING CAPSTAN

(71) Applicant: Ethicon LLC, Guaynabo, PR (US)

(72) Inventor: Eric N. Johnson, Maineville, OH (US)

(73) Assignee: Cilag GmbH International

( * ) Notice: Subject to any disclaimer, the term of this patent is extended or adjusted under 35 U.S.C. 154(b) by 141 days.

(21) Appl. No.: 16/377,806

(22) Filed: Apr. 8, 2019

(65) Prior Publication Data
US 2020/0315728 A1    Oct. 8, 2020

(51) Int. Cl.
| A61B 34/00 | (2016.01) |
| --- | --- |
| A61B 34/37 | (2016.01) |
| A61B 34/30 | (2016.01) |
| A61B 50/13 | (2016.01) |
| A61B 90/00 | (2016.01) |
| A61B 17/00 | (2006.01) |

(52) U.S. Cl.
CPC .............. *A61B 34/71* (2016.02); *A61B 34/37* (2016.02); *A61B 50/13* (2016.02); *A61B 90/361* (2016.02); *A61B 90/37* (2016.02); *A61B 2017/00323* (2013.01); *A61B 2017/00973* (2013.01); *A61B 2034/302* (2016.02); *A61B 2034/306* (2016.02); *A61B 2034/715* (2016.02); *A61B 2090/064* (2016.02)

(58) Field of Classification Search
CPC combination set(s) only.
See application file for complete search history.

(56) References Cited

U.S. PATENT DOCUMENTS

| 4,553,738 A * | 11/1985 | Plummer ................. B66D 3/16 254/134.3 FT |
| 2010/0082041 A1* | 4/2010 | Prisco .................... A61B 34/37 606/130 |
| 2014/0128849 A1* | 5/2014 | Au ......................... A61B 34/71 606/1 |

FOREIGN PATENT DOCUMENTS

| KR | 100 942 428 B1 | 2/2010 |
| WO | 2008046030 A2 | 4/2008 |
| WO | 2014070980 A1 | 5/2014 |

OTHER PUBLICATIONS

ISR/WO for related PCT application No. PCT/IB2020/052706 dated Jun. 30, 2020.

* cited by examiner

*Primary Examiner* — Tan-Uyen T Ho
*Assistant Examiner* — Bridget E. Rabaglia
(74) *Attorney, Agent, or Firm* — Vorys, Sater, Seymour and Pease LLP (57) ABSTRACT

A surgical tool includes a drive housing, a drive input and input shaft rotatably mounted to the drive housing, and a drive assembly mounted to the input shaft and including an upper capstan rotatably mounted to the input shaft with a first one-way bearing, and a lower capstan rotatably mounted to the input shaft with a second one-way bearing. First and second drive cables are coupled to the upper and lower capstans and extend to an end effector of the surgical tool. Rotating the input shaft in a first angular direction rotationally disengages the lower capstan from the input shaft and drives the upper capstan in the first angular direction, and rotating the input shaft in a second angular direction rotationally disengages the upper capstan from the input shaft and drives the lower capstan in the second angular direction.

20 Claims, 7 Drawing Sheets

SLACK CABLE ELIMINATING CAPSTAN

BACKGROUND

Minimally invasive surgical (MIS) instruments are often preferred over traditional open surgical devices due to reduced post-operative recovery time and minimal scarring. Laparoscopic surgery is one type of MIS procedure in which one or more small incisions are formed in the abdomen of a patient and a trocar is inserted through the incision to form a pathway that provides access to the abdominal cavity. Through the trocar, a variety of instruments and surgical tools can be introduced into the abdominal cavity. The instruments and tools introduced into the abdominal cavity via the trocar can be used to engage and/or treat tissue in a number of ways to achieve a diagnostic or therapeutic effect.

Various robotic systems have recently been developed to assist in MIS procedures and facilitate more instinctive hand movements by maintaining natural eye-hand axis. Such robotic systems can also allow for more degrees of freedom in movement by including an articulable "wrist" joint in the surgical tool that creates a more natural hand-like articulation. In such systems, an end effector positioned at the distal end of the surgical tool can be articulated (moved) using a cable driven motion system having one or more drive cables (or other elongate members) that extend through the wrist joint. A user (e.g., a surgeon) is able to remotely operate the end effector by grasping and manipulating in space one or more controllers that communicate with a tool driver coupled to the surgical instrument. User inputs are processed by a computer system incorporated into the robotic surgical system, and the tool driver responds by actuating the cable driven motion system and thereby actively controlling the tension balance in the drive cables. Moving the drive cables articulates the end effector to desired angular positions and configurations.

A number of mechanical and manufacturing hurdles must be overcome through component design and assembly to enable consistent and predictable performance of the end effector and its associated cable driven motion system.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

The present disclosure is related to robotic surgical systems and, more particularly, to capstan drive assemblies designed to eliminate slack in drive cables by ensuring a minimum cable tension is maintained.

Embodiments discussed herein describe surgical tools that include a drive housing having an elongate shaft extending therefrom and an end effector operatively coupled to a distal end of the elongate shaft. A drive input and input shaft are rotatably mounted to the drive housing, and a drive assembly is mounted to the input shaft and includes an upper capstan rotatably mounted to the input shaft with a first one-way bearing, and a lower capstan rotatably mounted to the input shaft with a second one-way bearing. A first drive cable is coupled to the upper capstan and extends to the end effector, and a second drive cable is coupled to the lower capstan and extends to the end effector. Rotating the input shaft in a first angular direction rotationally disengages the lower capstan from the input shaft and drives the upper capstan in the first angular direction to pull the first drive cable in a first linear direction. Rotating the input shaft in a second angular direction opposite the first angular direction rotationally disengages the upper capstan from the input shaft and drives the lower capstan in the second angular direction to pull the second drive cable in a second linear direction opposite the first linear direction.

Figure 1:
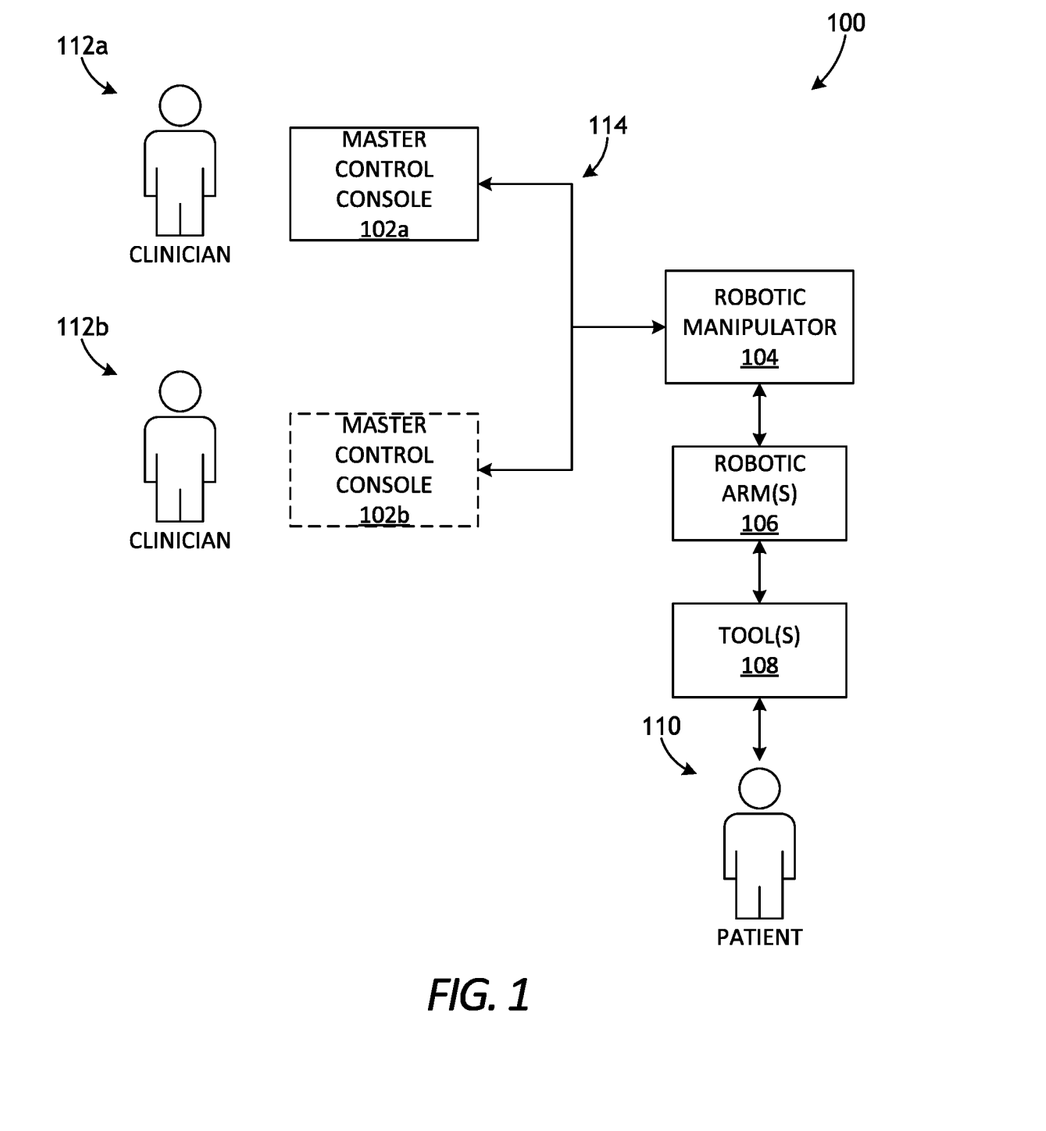
FIG. 1 is a block diagram of an example robotic surgical system that may incorporate some or all of the principles of the present disclosure.
Figure 2:
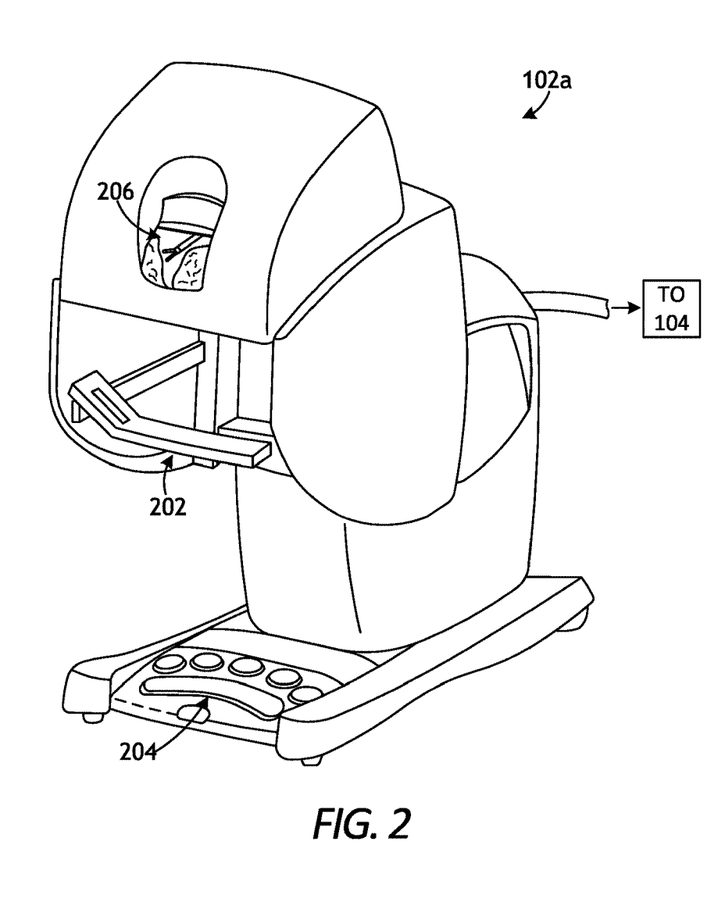
FIG. 2 is an example embodiment of one of the master control consoles of FIG. 1.
Figure 3:
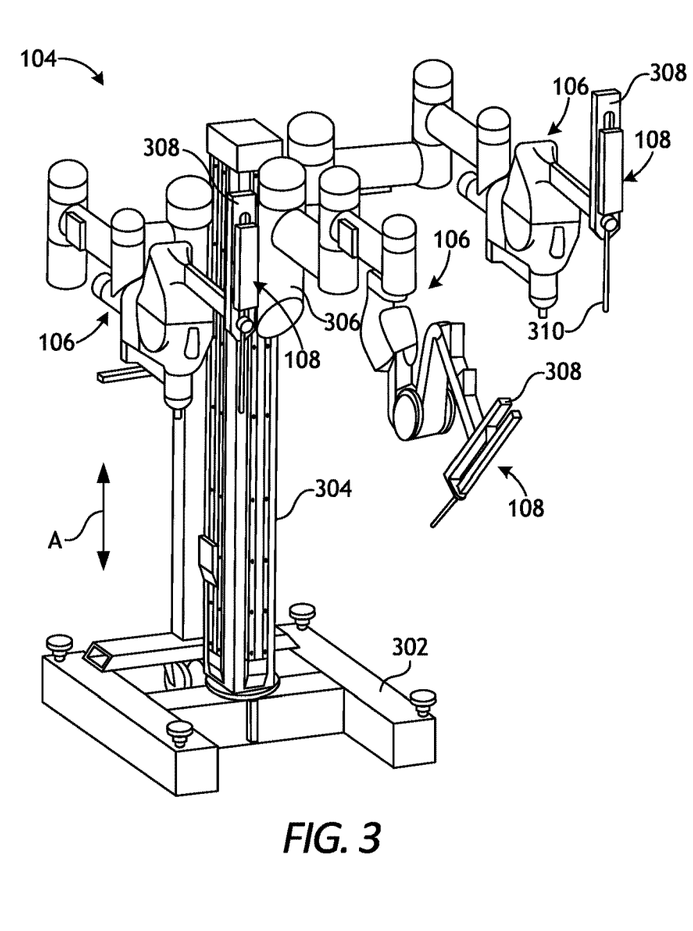
FIG. 3 depicts one example of the robotic manipulator of FIG. 1, according to one or more embodiments.

FIGS. 1-3 illustrate the structure and operation of an example robotic surgical system and associated components thereof. While applicable to robotic surgical systems, it is noted that the principles of the present disclosure may equally or alternatively be applied to non-robotic surgical systems, without departing from the scope of the disclosure.

FIG. 1 is a block diagram of an example robotic surgical system 100 that may incorporate some or all of the principles of the present disclosure. As illustrated, the system 100 can include at least one master control console 102a and at least one robotic manipulator 104. The robotic manipulator 104 may be mechanically and/or electrically coupled to or otherwise include one or more robotic arms 106. In some embodiments, the robotic manipulator 104 may be mounted to a transport cart (alternately referred to as an "arm cart") that enables mobility of the robotic manipulator 104 and the associated robotic arms 106. Each robotic arm 106 may include and otherwise provide a tool driver where one or more surgical instruments or tools 108 may be mounted for performing various surgical tasks on a patient 110. Operation of the robotic arms 106, the corresponding tool drivers, and the associated tools 108 may be directed by a clinician 112a (e.g., a surgeon) from the master control console 102a.

In some embodiments, a second master control console 102b (shown in dashed lines) operated by a second clinician 112b may also help direct operation of the robotic arms 106 and the tools 108 in conjunction with the first clinician 112a. In such embodiments, for example, each clinician 112a,b may control different robotic arms 106 or, in some cases, complete control of the robotic arms 106 may be passed between the clinicians 112a,b. In some embodiments, additional robotic manipulators having additional robotic arms may be utilized during surgery on a patient 110, and these additional robotic arms may be controlled by one or more of the master control consoles 102a,b.

The robotic manipulator 104 and the master control consoles 102a,b, may communicate with one another via a communications link 114, which may be any type of wired or wireless communications link configured to carry suitable types of signals (e.g., electrical, optical, infrared, etc.) according to any communications protocol. The communications link 114 may be an actual physical link or it may be a logical link that uses one or more actual physical links. When the link is a logical link the type of physical link may be a data link, uplink, downlink, fiber optic link, point-to-point link, for example, as is well known in the computer networking art to refer to the communications facilities that connect nodes of a network. Accordingly, the clinicians 112a,b may be able to remotely control the robotic arms 106 via the communications link 114, thus enabling the clinicians 112a,b to operate on the patient 110 remotely.

FIG. 2 is one example embodiment of the master control console 102a that may be used to control operation of the robotic manipulator 104 of FIG. 1. As illustrated, the master control console 102a can include a support 202 on which the clinician 112a,b (FIG. 1) can rest his/her forearms while gripping one or more user input devices (not shown). The user input devices can comprise, for example, physical controllers such as, but not limited to, a joystick, exoskeletal gloves, a master manipulator, etc., and may be movable in multiple degrees of freedom to control the position and operation of the surgical tool(s) 108 (FIG. 1). In some embodiments, the master control console 102a may further include one or more foot pedals 204 engageable by the clinician 112a,b to change the configuration of the surgical system and/or generate additional control signals to control operation of the surgical tool(s) 108.

The user input devices and/or the foot pedals 204 may be manipulated while the clinician 112a,b (FIG. 1) views the procedure via a visual display 206. Images displayed on the visual display 206 may be obtained from an endoscopic camera or "endoscope." In some embodiments, the visual display 206 may include or otherwise incorporate a force feedback meter or "force indicator" that provides the clinician 112a,b with a visual indication of the magnitude of force being assumed by the surgical tool (i.e., a cutting instrument or dynamic clamping member) and in which direction. As will be appreciated, other sensor arrangements may be employed to provide the master control console 102a with an indication of other surgical tool metrics, such as whether a staple cartridge has been loaded into an end effector or whether an anvil has been moved to a closed position prior to firing, for example.

FIG. 3 depicts one example of the robotic manipulator 104 that may be used to operate a plurality of surgical tools 108, according to one or more embodiments. As illustrated, the robotic manipulator 104 may include a base 302 that supports a vertically extending column 304. A plurality of robotic arms 106 (three shown) may be operatively coupled to the column 304 at a carriage 306 that can be selectively adjusted to vary the height of the robotic arms 106 relative to the base 302, as indicated by the arrow A.

The robotic arms 106 may comprise manually articulable linkages, alternately referred to as "set-up joints." In the illustrated embodiment, a surgical tool 108 is mounted to corresponding tool drivers 308 provided on each robotic arm 106. Each tool driver 308 may include one or more drivers or motors used to interact with a corresponding one or more drive inputs of the surgical tools 108, and actuation of the drive inputs causes the associated surgical tool 108 to operate.

One of the surgical tools 108 may comprise an image capture device 310, such as an endoscope, which may include, for example, a laparoscope, an arthroscope, a hysteroscope, or may alternatively include some other imaging modality, such as ultrasound, infrared, fluoroscopy, magnetic resonance imaging, or the like. The image capture device 310 has a viewing end located at the distal end of an elongate shaft, which permits the viewing end to be inserted through an entry port into an internal surgical site of a patient's body. The image capture device 310 may be communicably coupled to the visual display 206 (FIG. 2) and capable of transmitting images in real-time to be displayed on the visual display 206.

The remaining surgical tools may be communicably coupled to the user input devices held by the clinician 112a,b (FIG. 1) at the master control console 102a (FIG. 2). Movement of the robotic arms 106 and associated surgical tools 108 may be controlled by the clinician 112a,b manipulating the user input devices. As described in more detail below, the surgical tools 108 may include or otherwise incorporate an end effector mounted on a corresponding articulable wrist pivotally mounted on a distal end of an associated elongate shaft. The elongate shaft permits the end effector to be inserted through entry ports into the internal surgical site of a patient's body, and the user input devices also control movement (actuation) of the end effector.

In use, the robotic manipulator 104 is positioned close to a patient requiring surgery and is then normally caused to remain stationary until a surgical procedure to be performed has been completed. The robotic manipulator 104 typically has wheels or castors to render it mobile. The lateral and vertical positioning of the robotic arms 106 may be set by the clinician 112a,b (FIG. 1) to facilitate passing the elongate shafts of the surgical tools 108 and the image capture device 310 through the entry ports to desired positions relative to the surgical site. When the surgical tools 108 and image capture device 310 are so positioned, the robotic arms 106 and carriage 306 can be locked in position.

Figures 4, 5:
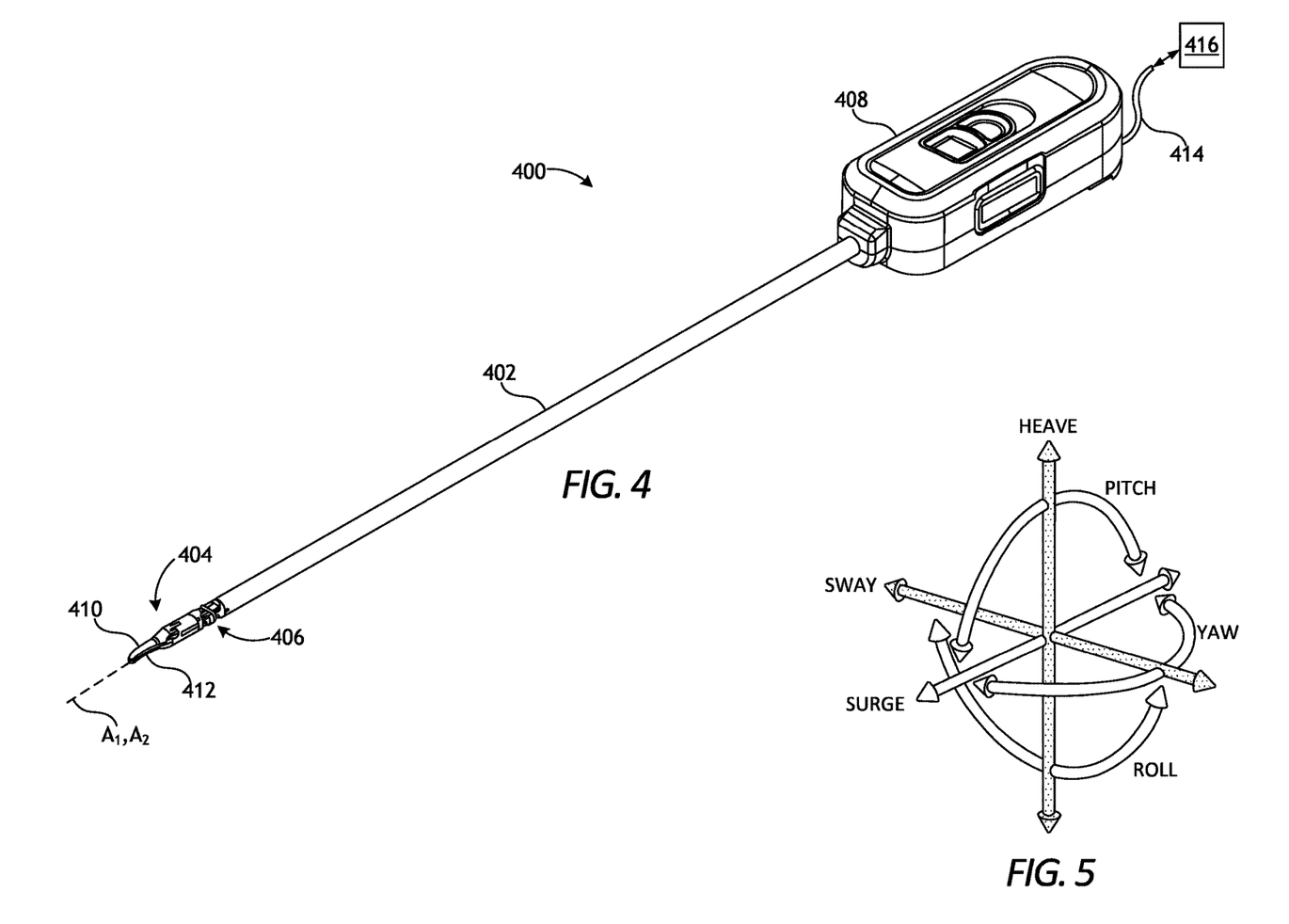
FIG. 4 is an isometric side view of an example surgical tool that may incorporate some or all of the principles of the present disclosure.
FIG. 5 illustrates potential degrees of freedom in which the wrist of FIG. 4 may be able to articulate (pivot).

FIG. 4 is an isometric side view of an example surgical tool 400 that may incorporate some or all of the principles of the present disclosure. The surgical tool 400 may be the same as or similar to the surgical tool(s) 108 of FIGS. 1 and 3 and, therefore, may be used in conjunction with a robotic surgical system, such as the robotic surgical system 100 of FIG. 1. Accordingly, the surgical tool 400 may be designed to be releasably coupled to a tool driver included in the robotic surgical system 100. In other embodiments, however, aspects of the surgical tool 400 may be adapted for use in a manual or hand-operated manner, without departing from the scope of the disclosure.

As illustrated, the surgical tool 400 includes an elongated shaft 402, an end effector 404, a wrist 406 (alternately referred to as a "wrist joint" or an "articulable wrist joint") that couples the end effector 404 to the distal end of the shaft 402, and a drive housing 408 coupled to the proximal end of the shaft 402. In applications where the surgical tool is used in conjunction with a robotic surgical system (e.g., the robotic surgical system 100 of FIG. 1), the drive housing 408 can include coupling features that releasably couple the surgical tool 400 to the robotic surgical system.

The terms "proximal" and "distal" are defined herein relative to a robotic surgical system having an interface configured to mechanically and electrically couple the surgical tool 400 (e.g., the housing 408) to a robotic manipulator. The term "proximal" refers to the position of an element closer to the robotic manipulator and the term "distal" refers to the position of an element closer to the end effector 404 and thus further away from the robotic manipulator. Alternatively, in manual or hand-operated applications, the terms "proximal" and "distal" are defined herein relative to a user, such as a surgeon or clinician. The term "proximal" refers to the position of an element closer to the user and the term "distal" refers to the position of an element closer to the end effector 404 and thus further away from the user. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

During use of the surgical tool 400, the end effector 404 is configured to move (pivot) relative to the shaft 402 at the wrist 406 to position the end effector 404 at desired orientations and locations relative to a surgical site. To accomplish this, the housing 408 includes (contains) various drive inputs and mechanisms (e.g., gears, actuators, etc.) designed to control operation of various features associated with the end effector 404 (e.g., clamping, firing, rotation, articulation, cutting, etc.). In at least some embodiments, the shaft 402, and hence the end effector 404 coupled thereto, is configured to rotate about a longitudinal axis $A_1$ of the shaft 402. In such embodiments, at least one of the drive inputs included in the housing 408 is configured to control rotational movement of the shaft 402 about the longitudinal axis $A_1$.

The surgical tool 400 can have any of a variety of configurations capable of performing at least one surgical function. For example, the surgical tool 400 may include, but is not limited to, forceps, a grasper, a needle driver, scissors, an electro cautery tool, a stapler, a clip applier, a hook, a spatula, a suction tool, an irrigation tool, an imaging device (e.g., an endoscope or ultrasonic probe), or any combination thereof. In some embodiments, the surgical tool 400 may be configured to apply energy to tissue, such as radio frequency (RF) energy. In the illustrated embodiment, the end effector 404 comprises a tissue grasper and vessel sealer that include opposing jaws 410, 412 configured to move (articulate) between open and closed positions. As will be appreciated, however, the opposing jaws 410, 412 may alternatively form part of other types of end effectors such as, but not limited to, a surgical scissors, a clip applier, a needle driver, a babcock including a pair of opposed grasping jaws, bipolar jaws (e.g., bipolar Maryland grasper, forceps, a fenestrated grasper, etc.), etc. One or both of the jaws 410, 412 may be configured to pivot to articulate the end effector 404 between the open and closed positions.

The shaft 402 is an elongate member extending distally from the housing 408 and has at least one lumen extending therethrough along its axial length. In some embodiments, the shaft 402 may be fixed to the housing 408, but could alternatively be rotatably mounted to the housing 408 to allow the shaft 402 to rotate about the longitudinal axis $A_1$. In yet other embodiments, the shaft 402 may be releasably coupled to the housing 408, which may allow a single housing 408 to be adaptable to various shafts having different end effectors.

FIG. 5 illustrates the potential degrees of freedom in which the wrist 406 may be able to articulate (pivot). The wrist 406 can have any of a variety of configurations. In general, the wrist 406 comprises a joint configured to allow pivoting movement of the end effector 404 relative to the shaft 402. The degrees of freedom of the wrist 406 are represented by three translational variables (i.e., surge, heave, and sway), and by three rotational variables (i.e., Euler angles or roll, pitch, and yaw). The translational and rotational variables describe the position and orientation of a component of a surgical system (e.g., the end effector 404) with respect to a given reference Cartesian frame. As depicted in FIG. 5, "surge" refers to forward and backward translational movement, "heave" refers to translational movement up and down, and "sway" refers to translational movement left and right. With regard to the rotational terms, "roll" refers to tilting side to side, "pitch" refers to tilting forward and backward, and "yaw" refers to turning left and right.

The pivoting motion can include pitch movement about a first axis of the wrist 406 (e.g., X-axis), yaw movement about a second axis of the wrist 406 (e.g., Y-axis), and combinations thereof to allow for 360° rotational movement of the end effector 404 about the wrist 406. In other applications, the pivoting motion can be limited to movement in a single plane, e.g., only pitch movement about the first axis of the wrist 406 or only yaw movement about the second axis of the wrist 406, such that the end effector 404 moves only in a single plane.

Referring again to FIG. 4, the surgical tool 400 may also include a plurality of drive cables (obscured in FIG. 4) that form part of a cable driven motion system configured to facilitate movement and articulation of the end effector 404 relative to the shaft 402. Moving (actuating) at least some of the drive cables moves the end effector 404 between an unarticulated position and an articulated position. The end effector 404 is depicted in FIG. 4 in the unarticulated position where a longitudinal axis $A_2$ of the end effector 404 is substantially aligned with the longitudinal axis $A_1$ of the shaft 402, such that the end effector 404 is at a substantially zero angle relative to the shaft 402. In the articulated position, the longitudinal axes $A_1$, $A_2$ would be angularly offset from each other such that the end effector 404 is at a non-zero angle relative to the shaft 402.

In some embodiments, the surgical tool 400 may be supplied with electrical power (current) via a power cable 414 coupled to the housing 408. In other embodiments, the power cable 414 may be omitted and electrical power may be supplied to the surgical tool 400 via an internal power source, such as one or more batteries or fuel cells. In such embodiments, the surgical tool 400 may alternatively be characterized and otherwise referred to herein as an "electrosurgical instrument" capable of providing electrical energy to the end effector 404.

The power cable 414 may place the surgical tool 400 in communication with a generator 416 that supplies energy, such as electrical energy (e.g., radio frequency energy), ultrasonic energy, microwave energy, heat energy, or any combination thereof, to the surgical tool 400 and, more particularly, to the end effector 404 to cauterize and/or coagulate tissue. Accordingly, the generator 416 may comprise a radio frequency (RF) source, an ultrasonic source, a direct current source, and/or any other suitable type of electrical energy source that may be activated independently or simultaneously.

Figure 6:
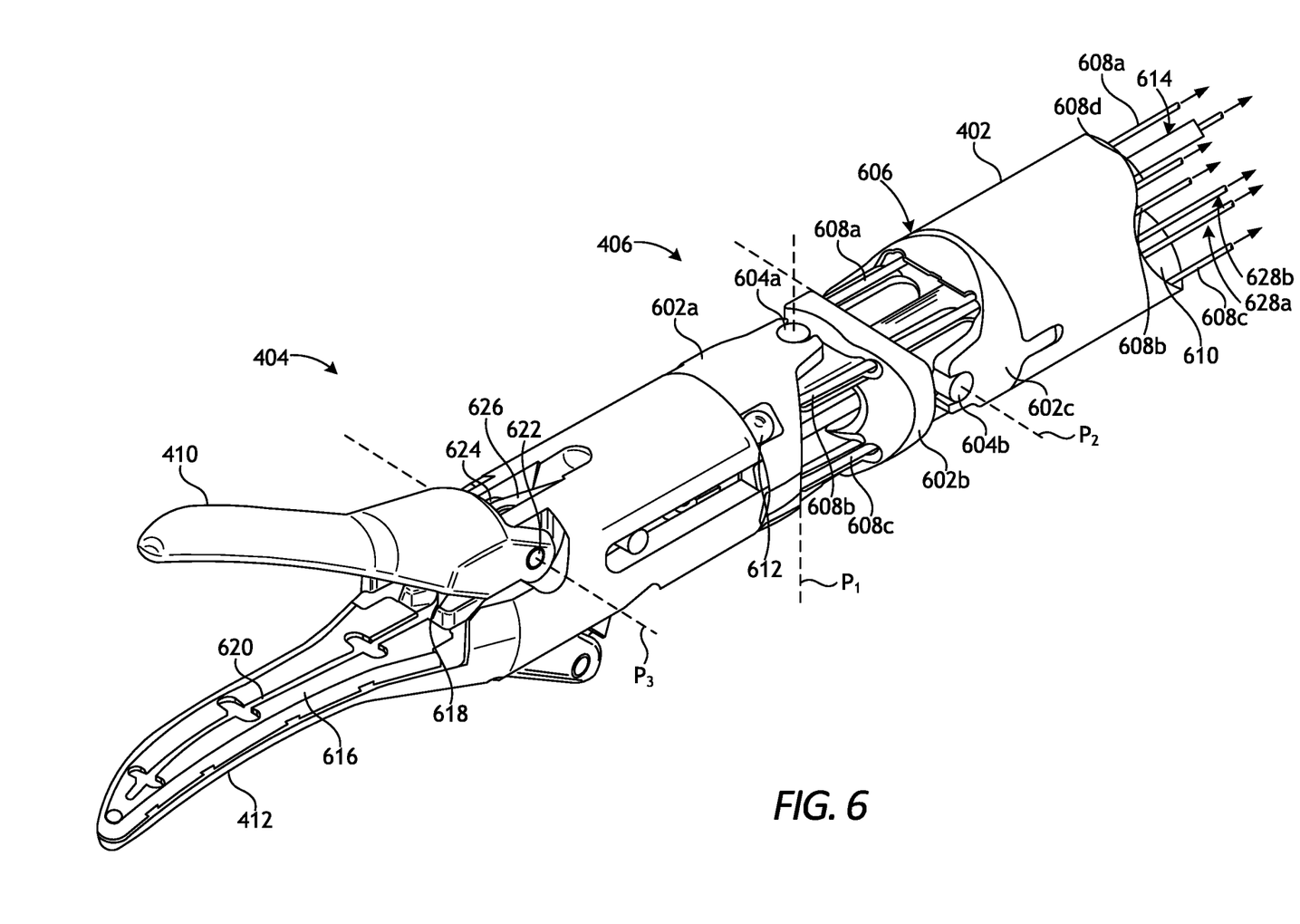
FIG. 6 is an enlarged isometric view of the distal end of the surgical tool of FIG. 4.

FIG. 6 is an enlarged isometric view of the distal end of the surgical tool 400 of FIG. 4. More specifically, FIG. 6 depicts enlarged views of the end effector 404 and the wrist 406, with the jaws 410, 412 of the end effector 404 in the open position. The wrist 406 operatively couples the end effector 404 to the shaft 402. In some embodiments, however, a shaft adapter may be directly coupled to the wrist 406 and otherwise interpose the shaft 402 and the wrist 406. Accordingly, the wrist 406 may be operatively coupled to the shaft 402 either through a direct coupling engagement where the wrist 406 is directly coupled to the distal end of the shaft 402, or an indirect coupling engagement where a shaft adapter interposes the wrist 406 and the distal end of the shaft 402. As used herein, the term "operatively couple" refers to a direct or indirect coupling engagement.

To operatively couple the end effector 404 to the shaft 402, the wrist 406 includes a first or "distal" linkage 602a, a second or "intermediate" linkage 602b, and a third or "proximal" linkage 602c. The linkages 602a-c are configured to facilitate articulation of the end effector 404 relative to the shaft 402, e.g., angle the end effector 404 relative to the longitudinal axis $A_1$ (FIG. 4) of the shaft 402. In the illustrated embodiment, articulation via the linkages 602a-c may be limited to pitch only, yaw only, or a combination thereof. As illustrated, the distal linkage 602a may be coupled to the end effector 404 and, more particularly, to the lower jaw 412 (or an extension of the lower jaw 412). The distal linkage 602a may also be rotatably coupled to the intermediate linkage 602b at a first axle 604a, and the intermediate linkage 602b may be rotatably coupled to the proximal linkage 602c at a second axle 604b. The proximal linkage 602c may then be coupled to a distal end 606 of the shaft 402 (or alternatively a shaft adapter).

The wrist 406 provides a first pivot axis $P_1$ that extends through the first axle 604a and a second pivot axis $P_2$ that extends through the second axle 604b. The first pivot axis $P_1$ is substantially perpendicular (orthogonal) to the longitudinal axis $A_2$ (FIG. 4) of the end effector 404, and the second pivot axis $P_2$ is substantially perpendicular (orthogonal) to both the longitudinal axis $A_2$ and the first pivot axis $P_1$. Movement about the first pivot axis $P_1$ provides "yaw" articulation of the end effector 404, and movement about the second pivot axis $P_2$ provides "pitch" articulation of the end effector 404. Alternatively, the first pivot axis $P_1$ could be configured to provide "pitch" articulation and the second pivot axis $P_2$ could be configured to provide "yaw" articulation.

A plurality of drive cables, shown as drive cables 608a, 608b, 608c, and 608d, extend longitudinally within a lumen 610 defined by the shaft 402 (and/or a shaft adaptor) and pass through the wrist 406 to be operatively coupled to the end effector 404. The lumen 610 can be a single lumen, as illustrated, or can alternatively comprise a plurality of independent lumens that each receive one or more of the drive cables 608a-d.

The drive cables 608a-d form part of the cable driven motion system briefly described above, and may be referred to and otherwise characterized as cables, bands, lines, cords, wires, ropes, strings, twisted strings, elongate members, etc. The drive cables 608a-d can be made from a variety of materials including, but not limited to, metal (e.g., tungsten, stainless steel, etc.), a polymer (e.g., ultra-high molecular weight polyethylene), a synthetic fiber (e.g., KEVLAR®, VECTRAN®, etc.), or any combination thereof. While four drive cables 608a-d are depicted in FIG. 6, more or less than four drive cables 608a-d may be included, without departing from the scope of the disclosure.

The drive cables 608a-d extend proximally from the end effector 404 to the drive housing 408 (FIG. 4) where they are operatively coupled to various actuation mechanisms (e.g., capstans) or devices housed therein to facilitate longitudinal movement (translation) of the drive cables 608a-d within the lumen 610. Selective actuation of all or a portion of the drive cables 608a-d causes the end effector 404 to articulate (pivot) relative to the shaft 402. More specifically, selective actuation causes a corresponding drive cable 608a-d to translate longitudinally within the lumen 610 and thereby cause pivoting movement of the end effector 404 at the wrist 406. Moving the drive cables 608a-d can be accomplished in a variety of ways, such as by triggering an associated actuator or mechanism (e.g., a capstan) operatively coupled to or housed within the drive housing 408 (FIG. 4). Moving a given drive cable 608a-d constitutes applying tension (i.e., pull force) to the given drive cable 608a-d in a proximal direction, which causes the given drive cable 608a-d to translate and thereby cause the end effector 404 to move (articulate) relative to the shaft 402. As will be appreciated, applying tension to and moving one drive cable 608a-d may result in the slackening of a drive cable 608a-d angularly (or diagonally) opposite to the moving drive cable 608a-d. Embodiments of the present disclosure may be configured to mitigate this occurrence.

The drive cables 608a-d each extend longitudinally through the first, second, and third linkages 602a-c and terminate at the first linkage 602a, thus operatively coupling each drive cable 608a-d to the end effector 404 and, more particularly, to the lower jaw 412. In some embodiments, as illustrated, the distal end of each drive cable 608a-d may include a ball crimp 612 (only one shown). In other embodiments, the distal end of each drive cable 608a-d may include a weld, an adhesive attachment, a press fit, or any combination of the foregoing.

In some embodiments, an electrical conductor 614 may supply electrical energy to the end effector 404 and, more particularly, to an electrode 616 included in the end effector 404. The electrical conductor 614 extends longitudinally within the lumen 610, through the wrist 406, and terminates at the electrode 616. The end effector 404 may be configured for monopolar or bipolar operation. In the illustrated embodiment, the electrode 616 is mounted to or otherwise forms part of the lower jaw 412. In other embodiments, however, the electrode 616 may form part of the upper jaw 410, or may alternatively be coupled to or form part of both jaws 410, 412. In some embodiments, the electrical conductor 614 and the power cable 414 (FIG. 4) may comprise the same structure. In other embodiments, however, the electrical conductor 614 may be electrically coupled to the power cable 414. In yet other embodiments, the electrical conductor 614 may extend to the drive housing 408 where it is electrically coupled to an internal power source, such as batteries or fuel cells.

In the illustrated embodiment, the end effector 404 comprises a vessel sealer that includes a knife or "cutting element" 618 (mostly occluded) configured to advance and retract within a groove or slot 620 defined longitudinally in one or both of the upper and lower jaws 410, 412. In example operation, the jaws 410, 412 may be actuated to close and grasp onto tissue, following which the cutting element 618 may be advanced distally along the slot(s) 620 to cut the grasped tissue. Alternatively, the cutting element 618 may be deployed after the application of electrical energy to transect coagulated tissue.

The jaws 410, 412 may be moved between the closed and open positions by pivoting the upper jaw 410 relative to the lower jaw 412. In the illustrated embodiment, the upper jaw 410 may be rotatably coupled (mounted) to the lower jaw 412 at a jaw axle 622. A third pivot axis $P_3$ extends through the jaw axle 622 and is generally perpendicular (orthogonal) to the first pivot axis $P_1$ and parallel to the second pivot axis $P_2$. A central pulley 624 (partially visible) may be mounted to the jaw axle 622 and receive a jaw cable 626 that may be actuated to selectively open and close the jaws 410, 412.

Similar to the drive cables 608a-d, the jaw cable 626 extends longitudinally within the lumen 610 and passes through the wrist 406. Moreover, the jaw cable 626 may form part of the cable driven motion system described herein and, therefore, may extend proximally from the end effector 404 to the drive housing 408 (FIG. 4). In some embodiments, the jaw cable 626 comprises two lines or wires connected at or near the central pulley 624 and extending proximally to the drive housing 408. In other embodiments, however, the jaw cable 626 may comprise a single line or wire looped around the central pulley 624 and opposing first and second ends 628a and 628b of the jaw cable 626 extend proximally to the drive housing 408.

Figure 7:
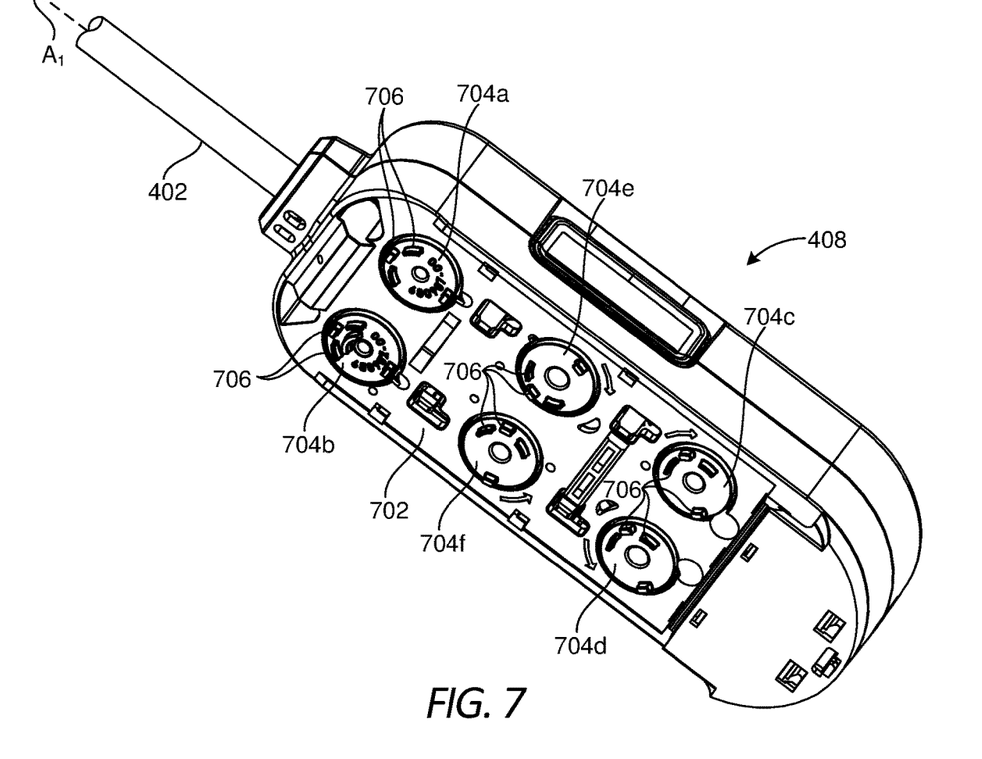
FIG. 7 is a bottom view of the drive housing of the surgical tool of FIG. 4.

FIG. 7 is a bottom view of the drive housing 408, according to one or more embodiments. As illustrated, the drive housing 408 may include a tool mounting interface 702 used to operatively couple the drive housing 408 to a tool driver of a robotic manipulator (e.g., the robotic manipulators 306, 502 of FIGS. 3 and 5, respectively). The tool mounting interface 702 may releasably couple the drive housing 408 to a tool driver in a variety of ways, such as by clamping thereto, clipping thereto, or slidably mating therewith. The tool mounting interface 702 may include an array of electrical connecting pins, which may be coupled to an electrical connection on the mounting surface of the tool driver. Accordingly, the tool mounting interface 702 may mechanically, magnetically, and/or electrically couple the drive housing 408 to the tool driver.

As illustrated, the interface 702 includes and supports a plurality of inputs, shown as drive inputs 704a, 704b, 704c, 704d, 704e, and 704f. Each drive input 704a-f may comprise a rotatable disc configured to align with and couple to a corresponding actuator of a given tool driver. Each drive input 704a-f may provide or define one or more surface features 706 configured to align and mate with corresponding features provided on the given actuator. The surface features 706 can include, for example, various protrusions and/or indentations that facilitate a mating engagement. Each of the drive inputs 704a-f may be actuated based on user inputs communicated to a tool driver coupled to the interface 702, and the user inputs may be received via a computer system incorporated into the robotic surgical system.

In some embodiments, actuation of the first drive input 704a may be configured to control rotation of the shaft 402 about its longitudinal axis $A_1$. The shaft 402 may be rotated clockwise or counter-clockwise depending on the rotational direction of the first drive input 704a. In some embodiments, actuation of the second drive input 704b may be configured to advance or retract the cutting element 618 (FIG. 6). In some embodiments, actuation of the third and fourth drive inputs 704c,d may be configured to open and close the jaws 410, 412 (FIGS. 4 and 6). More specifically, the first and second ends 628a,b (FIG. 6) of the jaw cable 626 (FIG. 6) may extend to and be operatively coupled to a corresponding one of the third and fourth drive inputs 704c,d such that cooperative actuation of the third and fourth drive inputs 704c,d causes the jaw cable 626 to open/close the jaws 410, 412.

In some embodiments, actuation of the fifth and sixth drive inputs 704e,f may be configured to axially translate the drive cables 608a-d (FIG. 6), and thereby articulate the end effector 404 (FIGS. 4 and 6). More specifically, two drive cables 608a-d may be operatively coupled to each drive input 704e,f such that actuation of the fifth drive input 704e causes two drive cables 608a-d to axially translate, and actuation of the sixth drive input 704f causes the other two drive cables 608a-d to axially translate. In one embodiment, for example, the second and third drive cables 608b,c may be driven by actuation of the fifth drive input 704e, and the first and fourth drive cables 608a,d may be driven by actuation of the sixth drive input 704e.

Figure 8:
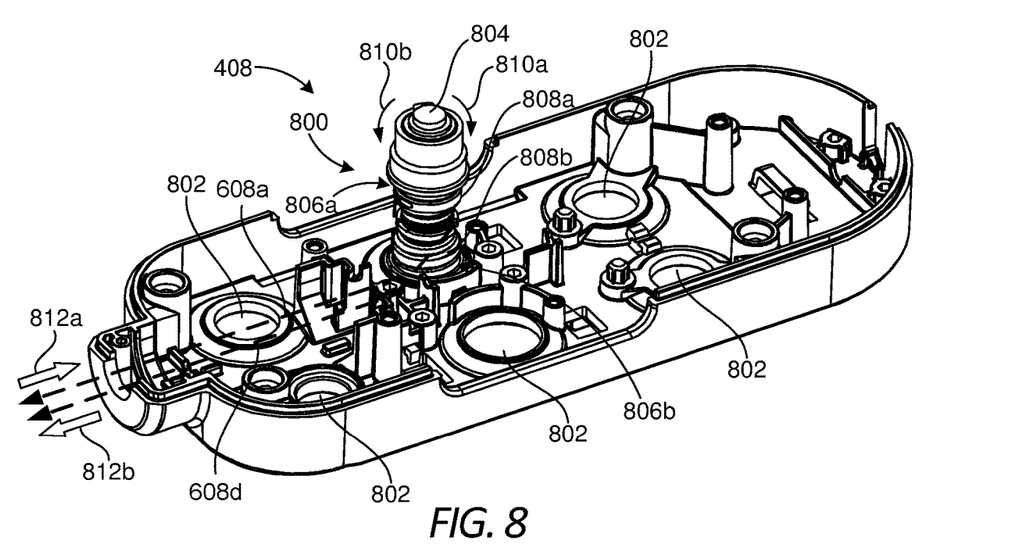
FIG. 8 is an isometric exposed view of the interior of the drive housing of the surgical tool of FIG. 6.

FIG. 8 is an isometric exposed view of the interior of the drive housing 408, according to one or more embodiments. Several component parts that would otherwise be contained within the drive housing 408 are not shown in FIG. 8 to enable discussion of the depicted component parts. More particularly, FIG. 8 depicts a drive assembly 800 associated with the sixth drive input 704f (FIG. 7), and several holes 802 are defined in the drive housing 408 where additional drive assemblies (not shown) would otherwise be mounted to the drive housing 408 and associated with the first-fifth drive inputs 704a-e, respectively.

The drive assembly 800 may include or otherwise be mounted to an input shaft 804. The input shaft 804 is operatively coupled to or otherwise extends from the sixth drive input 704f (FIG. 7) such that actuation of the sixth drive input 704f correspondingly rotates the input shaft 804.

The drive assembly 800 may also include a first or "upper" capstan assembly 806a and a second or "lower" capstan assembly 806b, and each capstan assembly 806a,b may be rotatably mounted to the input shaft 804. The upper capstan assembly 806a includes a first or "upper" capstan 808a and the lower capstan assembly 806b includes a second or "lower" capstan 808b. Each of the capstans 808a,b may have a drive cable coupled thereto (i.e., wrapped thereabout) and extending therefrom. In the illustrated embodiment, the first drive cable 608a (shown as dashed line) is coupled to the upper capstan 808a and the fourth drive cable 608d (shown as dashed line) is coupled to the lower capstan 808a. Each drive cable 608a,d extends from the corresponding capstan 808a,b and out of the drive housing 408. As will be appreciated, the first and fourth drive cables 608a,d may alternatively be coupled to the opposite capstan 808a,b, without departing from the scope of the disclosure. Moreover, any combination of two of the drive cables 608a-d of FIG. 6 may be coupled to the capstans 808a,b, in accordance with this disclosure.

The upper capstan 808a may be operatively coupled to the input shaft 804 such that rotating the input shaft 804 in a first angular direction 810a (e.g., clockwise) correspondingly drives the upper capstan 808a in the first angular direction 810a, which causes the first drive cable 608a to be pulled in a first linear direction 812a (e.g., proximally) and correspondingly wrap about the upper capstan 808a. Moreover, rotating the input shaft 804 in the first angular direction 810a will rotationally disengage the lower capstan 808b from the input shaft 804 and allow the input shaft 804 to rotate relative to the lower capstan 808b. Consequently, when the input shaft 804 is rotated in the first angular direction 810a, the fourth drive cable 608d may be allowed to move in a second linear direction 812b (e.g., distally) opposite the first linear direction 812a, if needed, and may otherwise unwrap from the lower capstan 808b to help maintain adequate tensile load. In at least one embodiment, the length (linear distance) of the first drive cable 608a wrapped onto the upper capstan 808a when the input shaft 804 rotates in the first angular direction 810a may be substantially the same length (linear distance) of the fourth drive cable 608d unwrapped from the lower capstan 808b.

Conversely, the lower capstan 808b may be operatively coupled to the input shaft 804 such that rotating the input shaft 804 in a second angular direction 810b (e.g., counterclockwise) opposite the first angular direction 810a correspondingly drives the lower capstan 808b in the second angular direction 810a, which causes the fourth drive cable 608d to be pulled in the first linear direction 812a and correspondingly wrap about the lower capstan 808b. Moreover, rotating the input shaft 804 in the second angular direction 810b will rotationally disengage the upper capstan 808a from the input shaft 804, thus allowing the input shaft 804 to rotate relative to the upper capstan 808a. Consequently, when the input shaft 804 is rotated in the second angular direction 810b, the first drive cable 608a may be allowed to move in the second linear direction 812b, if needed, and may otherwise unwrap from the upper capstan 808a to help maintain adequate tensile load. In at least one embodiment, the length (linear distance) of the fourth drive cable 608b wrapped onto the lower capstan 808b when the input shaft 804 rotates in the second angular direction 810b may be substantially the same length (linear distance) of the first drive cable 608a unwrapped from the upper capstan 808a.

Figure 9A:
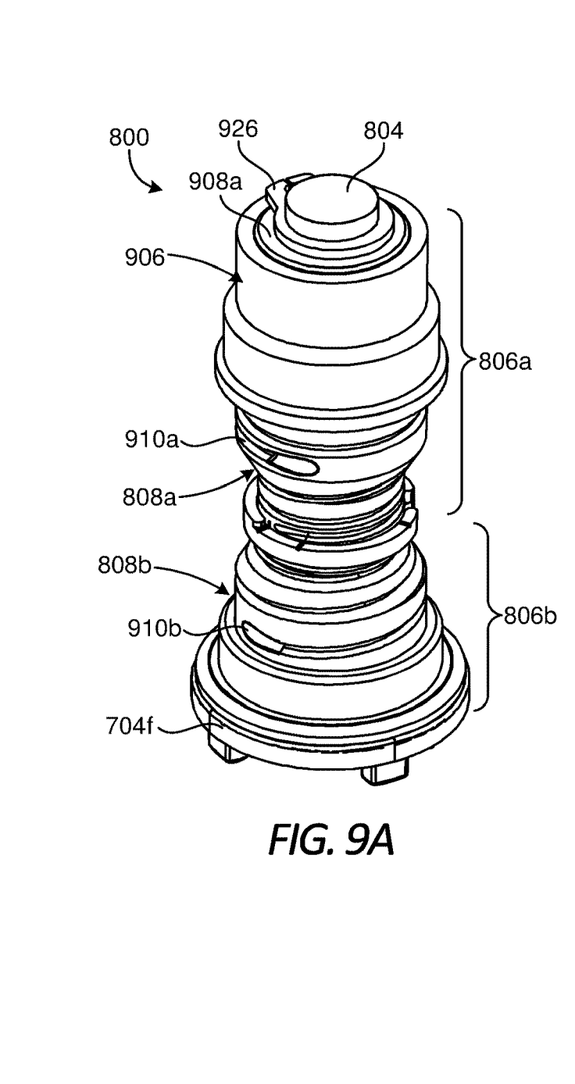
FIGS. 9A and 9B are enlarged isometric and exploded views of the drive assembly of FIG. 8, according to one or more embodiments of the disclosure.
Figure 9B:
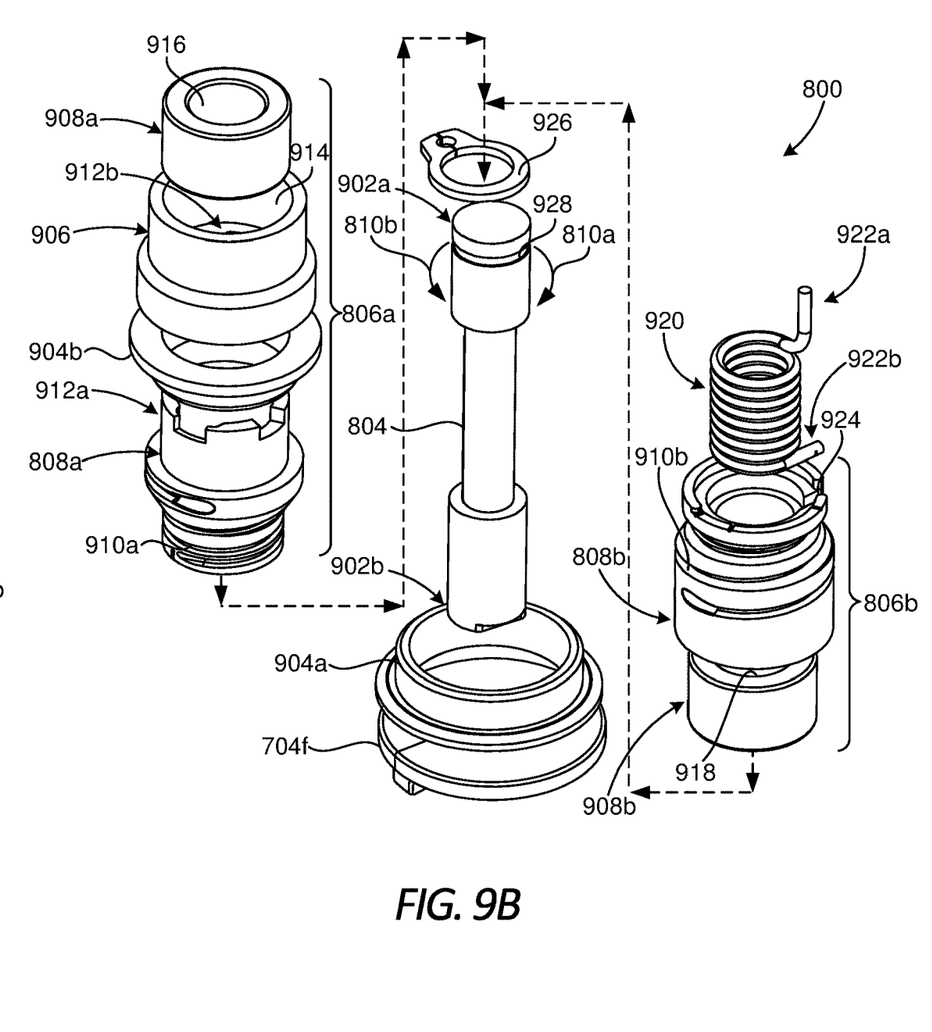

FIGS. 9A and 9B are enlarged isometric and exploded views of the drive assembly 800, according to one or more embodiments of the disclosure. As illustrated, the input shaft 804 comprises a generally elongate body having a first or upper end 902a and a second or lower end 902b opposite the upper end 902a. The sixth drive input 704f may be operatively coupled to the lower end 902b. In some embodiments, for example the sixth drive input 704f may be mechanically fastened to the lower end 902b, such as with a screw or the like. Alternatively, the input shaft 804 may form an integral extension of the sixth drive input 704f. The drive assembly 800 may also include a flanged bushing 904a configured to help rotatably mount the sixth drive input 704f to the drive housing 408 (FIGS. 4, 7, and 8). The flanged bushing 904a, however, may be optional.

In the illustrated embodiment, the upper capstan assembly 806a may include the upper capstan 808a, an adapter or housing 906, and a first one-way bearing 908a (best seen in FIG. 9B). As illustrated, the upper capstan 808a includes a first helical groove 910a that extends about the outer circumference of at least a portion of the upper capstan 808a. The first helical groove 910a may be configured to receive a drive cable, such as the first drive cable 608a (FIGS. 6 and 8), as described above. The end of the first drive cable 608a may be fixedly attached to the upper capstan 808a, and as the upper capstan 808a rotates, the first drive cable 608a may be paid out (i.e., unwrapped) or pulled in, depending on the rotational direction.

The upper capstan 808a may be matable with the adapter 906. In some embodiments, as best seen in FIG. 9B, the upper capstan 808a may provide or otherwise define a first mating structure 912a and the adapter 906 may provide or otherwise define a second mating structure 912b (partially visible in FIG. 9B) matable with the first mating structure 912a. Upon appropriately mating the first and second mating structures 912a,b, the upper capstan 808a and the adapter 906 will rotate as a single, monolithic body. The first and second mating structures 912a,b may comprise any matable engagement that rotationally fixes the upper capstan 808a to the adapter 906, and vice versa. In the illustrated embodiment, the first and second mating structures 912a,b are matable castellations or castellated (interlocking) features defined on each component part. In other embodiments, however, the first and second mating structures 912a,b may alternately comprise a dovetail engagement, a tongue and groove engagement, a pin or clip engaged with mating holes, a splined engagement, an interference or shrink fit engagement, welding, an adhesive bonding, or any combination thereof.

In at least one embodiment, the upper capstan assembly 806a may further include a flanged bushing 904b that may help the upper capstan 808a mate with the adapter 906. In other embodiments, however, the flanged bushing 904b may be omitted, without departing from the scope of the disclosure. The flanged bushing 904b acts as a flanged plane bearing to mitigate friction between the upper capstan 808a and a frame structure (not illustrated) arranged within the drive housing 408 (FIG. 4) to support the upper capstan 808a.

The adapter 906 may define a cavity 914 sized to receive the first one-way bearing 908a. The first one-way bearing 908a may comprise any type of bearing that allows rotation in one angular direction, but prevents rotation in the opposite direction. The first one-way bearing 908a may comprise, for example, a one-way clutch bearing, a sprag-style bearing, an anti-reverse bearing, or any combination thereof. In at least one embodiment, the first one-way bearing 908a may comprise a ratchet mechanism that allows rotation in a first direction but prohibits rotation in a second direction. The first one-way bearing 908a may be secured within the cavity 914 via a variety of attachment means including, but not limited to, an interference fit, a mechanical attachment, a weld, an adhesive, or any combination thereof. When the upper capstan assembly 806a is assembled on the input shaft 704, an inner radial surface 916 of the first one-way bearing 908a may be positioned to engage an outer radial surface of the input shaft 704 at or near the upper end 902a.

Accordingly, in at least one embodiment, the upper capstan 808a may be rotatably mounted to the input shaft 804 via the adapter 906 and the first one-way bearing 908a. In other embodiments, however, the adapter 906 may be omitted from the upper capstan assembly 806a. In such embodiments, the first one-way bearing 908a may alternatively be secured to the upper capstan 808a.

In some embodiments, the first one-way bearing 908a may be non-rotatable in the first angular direction 810a, but may allow rotation in the second angular direction 810b. Consequently, when the input shaft 804 is rotated in the first angular direction 810a, the first one-way bearing 908a may bind against the input shaft 804 and transfer the torque from the input shaft 804 to the upper capstan 808a, and thereby drive the upper capstan 808a in the first angular direction 810a. As mentioned above, rotating the upper capstan 808a in the first angular direction 810a may cause the first drive cable 608a (FIGS. 6 and 8) to wrap about the upper capstan 808a. When the input shaft 804 is rotated in the second angular direction 810b, however, the first one-way bearing 908a may allow free motion that rotationally disengages the upper capstan 808a from the input shaft 804 and thereby allows the input shaft 804 to rotate relative to the upper capstan 808a.

The lower capstan assembly 806b may include the lower capstan 808b and a second one-way bearing 908b (best seen in FIG. 9B). As illustrated, the lower capstan 808b includes a second helical groove 910b that extends about the outer circumference of at least a portion of the lower capstan 808b. The second helical groove 910b may be configured to receive a drive cable, such as the fourth drive cable 608d (FIGS. 6 and 8), as described above. The end of the fourth drive cable 608d may be fixedly attached to the lower capstan 808b and, as the lower capstan 808b rotates, the fourth drive cable 608d may be paid out (i.e., unwrapped) or pulled in, depending on the rotational direction.

The second one-way bearing 908b may be operatively coupled to the lower capstan 808b. In one embodiment, for example, the second one-way bearing 908b may be received within a cavity (not shown) defined by the lower capstan 808b, and may be secured within the cavity via an interference fit, a mechanical attachment, a weld, an adhesive, or any combination thereof. When the lower capstan assembly 806b is assembled on the input shaft 704, an inner radial surface 918 of the second one-way bearing 908b may be positioned to engage an outer radial surface of the input shaft 704 at or near the upper end 902a.

Similar to the first one-way bearing 908a, the second one-way bearing 908b may comprise any type of bearing that allows rotation in one angular direction, but prevents rotation in the opposite direction. In at least one embodiment, the first and second one-way bearings 908a,b may be the same type of bearing, but mounted oppositely such that the first and second capstans 808a,b are driven in rotation by opposite angular rotation of the input shaft 804.

Accordingly, the lower capstan 808b may be rotatably mounted to the input shaft 804 via the second one-way bearing 908b. In some embodiments, the second one-way bearing 908b may be non-rotatable in the second angular direction 810b, but may allow rotation in the first angular direction 810a. Consequently, when the input shaft 804 is rotated in the second angular direction 810b, the second one-way bearing 908b may bind against the input shaft 804 and transfer the torque from the input shaft 804 to the lower capstan 808b, and thereby drive the lower capstan 808b in the second angular direction 810b. As mentioned above, rotating the lower capstan 808b in the second angular direction 810b may cause the fourth drive cable 608d (FIGS. 6 and 8) to wrap about the lower capstan 808b. When the input shaft 804 is rotated in the first angular direction 810a, however, the second one-way bearing 908b may allow free motion that rotationally disengages the lower capstan 808b from the input shaft 804 and allows the input shaft 804 to rotate relative to the lower capstan 808b.

The drive assembly 800 may further include a compliant member 920 operatively coupled to and extending between the upper and lower capstan assemblies 806a,b. In the illustrated embodiment, the compliant member 920 comprises a coil spring, but could alternatively comprise any other type of biasing device capable of transferring torque. For example, the compliant member 920 could alternately comprise a compression spring attached to each capstan assembly 806a,b with a cable. As illustrated, the compliant member 920 may have a first or upper end 922a engageable with the upper capstan assembly 806a, and a second or lower end 922b engageable with the lower capstan assembly 806b. In some embodiments, the upper end 922a may be configured to mate with a receiving feature (see FIG. 10) defined on the adapter 906. In other embodiments, however, the receiving feature may alternatively form part of the upper capstan 808a, without departing from the scope of the disclosure. Receiving the upper end 922a within the receiving feature may allow the compliant member 920 to transmit torque to the upper capstan assembly 806a and, more particularly, to the upper capstan 808a.

The lower end 922b of the compliant member 920 may be coupled to the lower capstan 808b. More particularly, the lower end 922b may extend laterally and be received within a slot 924 defined in the lower capstan 808b. In at least one embodiment, the bottom end of the upper capstan 808a may help keep the lower end 922b within the slot 924 when the drive assembly 800 is assembled. Receiving the lower end 922b within the slot 924 may allow the compliant member 920 to transmit torque to the lower capstan assembly 806b and, more particularly, to the lower capstan 808b.

Figure 10:
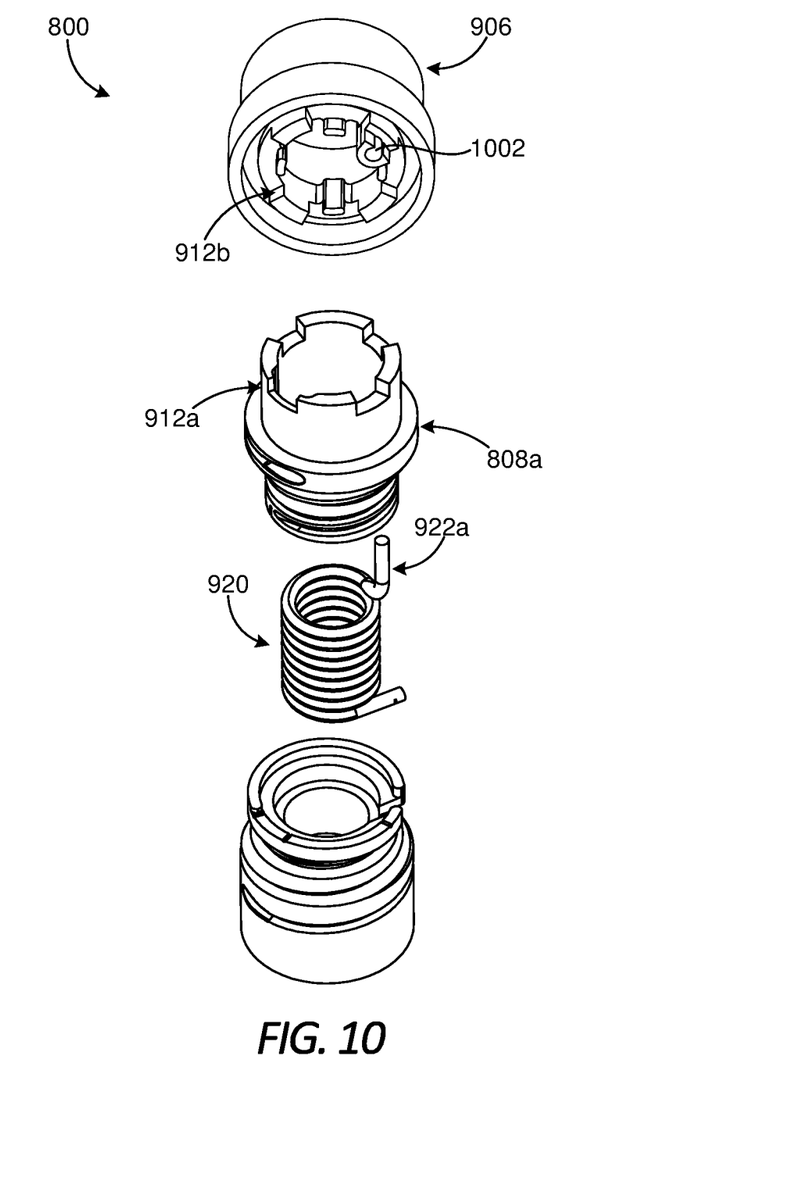
FIG. 10 is an exploded isometric view of a portion of the drive assembly of FIG. 8, according to one or more embodiments.

FIG. 10 is an exploded isometric view of a portion of the drive assembly 800, according to one or more embodiments. More specifically, FIG. 10 shows a bottom portion of the adapter 906. As mentioned above, the adapter 906 may define the second mating structure 912b, which is matable with the first mating structure 912a of the upper capstan 808a. Moreover, the adapter 906 may provide or define a receiver feature 1002 configured to receive and otherwise mate with the upper end 922a of the compliant member 920. As illustrated, the receiver feature 1002 may comprise a hole or cavity sized to receive the upper end 922a, but could alternatively comprise a slot or the like. In embodiments where the adapter 906 is omitted, however, the receiver feature 1002 may alternatively be provided on the upper capstan 808a, or the upper end 922a of the compliant member 920 may otherwise be coupled directly to the upper capstan 808a and capable of transferring torsion to the upper capstan assembly 806a.

Referring again to FIGS. 9A-9B, the compliant member 920 may be configured to provide a constant amount of opposing torsional load on the upper and lower capstan assemblies 806a,b to help reduce the amount of cable slack that might develop in the drive cables coupled thereto. The compliant member 920 may be pretensioned during assembly of the drive assembly 800, which causes the compliant member 920 to act on both the upper and lower capstan assemblies 806a,b in opposite angular directions and thereby urge the corresponding upper and lower capstans 808a,b to counter-rotate. In some embodiments, the torque provided by the compliant member 920 may be set at or below the pre-tension limit of the cables attached to the upper and lower capstans 808a,b. Consequently, if the tension in a given cable drops below the pre-tension value, the compliant member 920 will act on the corresponding capstan 808a,b and cause the capstan 808a,b to counter rotate and remove the slack.

During example operation, when the upper capstan 808a is rotated to pull on the first drive cable 608a (FIGS. 6 and 8), as described above, the tension on the fourth drive cable 608d (FIGS. 6 and 8) may slacken. The torsional load provided by the compliant member 920 on the lower capstan 808b, however, may counter-rotate the lower capstan 808b and thereby help remove this slack in the fourth drive cable 608d. Conversely, when the lower capstan 808b is rotated to pull on the fourth drive cable 608d, as described above, the tension on the first drive cable 608a may slacken, but the torsional load provided by the compliant member 920 on the upper capstan 808a may counter-rotate the upper capstan 808a and thereby help remove any slack developing in the first drive cable 608a. Accordingly, this creates a system that is very stiff when applying tension to cables, and the system is therefore able to resist external loads applied during a surgical procedure.

Still referring to FIGS. 9A-9B, after assembling the upper and lower capstan assemblies 806a,b on the input shaft 804, a lock ring 926 may be secured to the input shaft 804 at or near the upper end 902a to secure the capstan assemblies 806a,b to the input shaft 804. In some embodiments, the lock ring 926 may be sized to fit within an annular groove 928 (FIG. 9B) defined on the outer surface of the input shaft 804. As will be appreciated, the lock ring 926 may be replaced with any device or mechanism that may suitably maintain the upper and lower capstan assemblies 806a,b mounted to the input shaft 804, without departing from the scope of the disclosure.

Embodiments disclosed herein include:

A. A surgical tool that includes a drive housing having an elongate shaft extending therefrom, an end effector operatively coupled to a distal end of the elongate shaft, a drive input and input shaft rotatably mounted to the drive housing, a drive assembly mounted to the input shaft and including an upper capstan rotatably mounted to the input shaft with a first one-way bearing, and a lower capstan rotatably mounted to the input shaft with a second one-way bearing, and a first drive cable coupled to the upper capstan and extending to the end effector, and a second drive cable coupled to the lower capstan and extending to the end effector, wherein rotating the input shaft in a first angular direction rotationally disengages the lower capstan from the input shaft and drives the upper capstan in the first angular direction to pull the first drive cable in a first linear direction, and wherein rotating the input shaft in a second angular direction opposite the first angular direction rotationally disengages the upper capstan from the input shaft and drives the lower capstan in the second angular direction to pull the second drive cable in a second linear direction opposite the first linear direction.

B. A method of operating a surgical tool includes positioning the surgical tool adjacent a patient for operation, the surgical tool including a drive housing having an elongate shaft extending therefrom and an end effector operatively coupled to a distal end of the elongate shaft, a drive input and input shaft rotatably mounted to the drive housing, a drive assembly mounted to the input shaft and including an upper capstan rotatably mounted to the input shaft with a first one-way bearing, and a lower capstan rotatably mounted to the input shaft with a second one-way bearing, and a first drive cable coupled to the upper capstan and extending to the end effector, and a second drive cable coupled to the lower capstan and extending to the end effector. The method further including actuating the drive input to rotate the input shaft in a first angular direction and thereby driving the upper capstan in the first angular direction to pull the first drive cable in a first linear direction, rotationally disengaging the lower capstan from the input shaft when the input shaft rotates in the first angular direction, actuating the drive input to rotate the input shaft in a second angular direction opposite the first angular direction and thereby driving the lower capstan in the second angular direction to pull the second drive cable in a second linear direction opposite the first linear direction, and rotationally disengaging the upper capstan from the input shaft when the input shaft rotates in the second angular direction.

C. A drive assembly for a surgical tool that includes a first capstan assembly including an upper capstan rotatably mountable to an input shaft of the surgical tool with a first one-way bearing, a lower capstan assembly including a lower capstan rotatably mountable to the input shaft with a second one-way bearing, a compliant member operatively coupled to and extending between the upper and lower capstan assemblies, wherein the compliant member provides constant opposing torsional loads on the upper and lower capstan assemblies that urge the upper and lower capstans to counter-rotate, and a first drive cable securable to the upper capstan and extendable to an end effector of the surgical tool, and a second drive cable securable to the lower capstan and extendable to the end effector, wherein rotating the input shaft in a first angular direction rotationally disengages the lower capstan from the input shaft and drives the upper capstan in the first angular direction to pull the first drive cable in a first linear direction, and wherein rotating the input shaft in a second angular direction opposite the first angular direction rotationally disengages the upper capstan from the input shaft and drives the lower capstan in the second angular direction to pull the second drive cable in a second linear direction opposite the first linear direction.

Each of embodiments A, B, and C may have one or more of the following additional elements in any combination: Element 1: wherein rotating the input shaft in the first angular direction allows the second drive cable to unwind from the lower capstan and move in the second linear direction, and wherein rotating the input shaft in the second angular direction allows the first drive cable to unwind from the upper capstan and move in the first linear direction. Element 2: further comprising a compliant member operatively coupled to and extending between the upper and lower capstans, wherein the compliant member provides constant opposing torsional loads on the upper and lower capstans that urge the upper and lower capstans to counter-rotate. Element 3: wherein the compliant member is pretensioned during assembly to provide a torque at or below a pretension limit of the first and second drive cables. Element 4: wherein the first one-way bearing is secured to an adapter and the adapter is matable with the upper capstan such that rotation of the adapter correspondingly rotates the upper capstan. Element 5: wherein the adapter and the upper capstan each provide matable interlocking features. Element 6: wherein the adapter defines a cavity sized to receive the first one-way bearing. Element 7: wherein the first one-way bearing is secured to the upper capstan. Element 8: wherein the first and second one-way bearings are selected from the group consisting of a one-way clutch bearing, a sprag-style bearing, an anti-reverse bearing, a ratchet mechanism, and any combination thereof.

Element 9: further comprising allowing the second drive cable to unwind from the lower capstan and move in the second linear direction when the input shaft is rotated in the first angular direction, and allowing the first drive cable to unwind from the upper capstan and move in the first linear direction when the input shaft is rotated in the second angular direction. Element 10: further comprising wrapping a first length of the first drive cable onto the upper capstan when the input shaft rotates in the first angular direction and simultaneously unwrapping a second length of the second drive cable from the lower capstan, wherein the first and second lengths are the same. Element 11: further comprising providing constant opposing torsional loads on the upper and lower capstans with a compliant member operatively coupled to and extending between the upper and lower capstans. Element 12: further comprising urging the upper and lower capstans to counter-rotate with the compliant member. Element 13: further comprising pretensioning the compliant member during assembly and thereby providing a torque at or below a pre-tension limit of the first and second drive cables. Element 14: wherein driving the upper capstan in the first angular direction further comprises removing slack in the second drive cable with the compliant member acting on the lower capstan, and wherein driving the lower capstan in the second angular direction further comprises removing slack in the first drive cable with the compliant member acting on the upper capstan.

Element 15: wherein rotating the input shaft in the first angular direction allows the second drive cable to unwind from the lower capstan and move in the second linear direction, and wherein rotating the input shaft in the second angular direction allows the first drive cable to unwind from the upper capstan and move in the first linear direction. Element 16: wherein the first capstan assembly further includes an adapter matable with the upper capstan such that rotation of the adapter correspondingly rotates the upper capstan, and wherein the first one-way bearing is secured to the adapter. Element 17: wherein the first and second one-way bearings are selected from the group consisting of a one-way clutch bearing, a sprag-style bearing, an anti-reverse bearing, a ratchet mechanism, and any combination thereof.

By way of non-limiting example, exemplary combinations applicable to A, B, and C include: Element 2 with Element 3; Element 4 with Element 5; Element 4 with Element 6; Element 9 with Element 10; Element 11 with Element 12; Element 11 with Element 13; and Element 11 with Element 14.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:

1. A surgical tool, comprising:
a drive housing having an elongate shaft extending therefrom;
an end effector operatively coupled to a distal end of the elongate shaft;
a drive input and input shaft rotatably mounted to the drive housing;
a drive assembly mounted to the input shaft and including an upper capstan rotatably mounted to the input shaft with a first one-way bearing, and a lower capstan rotatably mounted to the input shaft with a second one-way bearing; and
a first drive cable coupled to the upper capstan and extending to the end effector, and a second drive cable coupled to the lower capstan and extending to the end effector,
wherein rotating the input shaft in a first angular direction rotationally disengages the lower capstan from the input shaft and drives the upper capstan in the first angular direction to pull the first drive cable in a first linear direction, and
wherein rotating the input shaft in a second angular direction opposite the first angular direction rotationally disengages the upper capstan from the input shaft and drives the lower capstan in the second angular direction to pull the second drive cable in the first linear direction.

2. The surgical tool of claim 1, wherein rotating the input shaft in the first angular direction allows the second drive cable to unwind from the lower capstan and move in a second linear direction opposite the first linear direction, and wherein rotating the input shaft in the second angular direction allows the first drive cable to unwind from the upper capstan and move in the first second linear direction.

3. The surgical tool of claim 1, further comprising a compliant member operatively coupled to and extending between the upper and lower capstans, wherein the compliant member provides constant opposing torsional loads on the upper and lower capstans that urge the upper and lower capstans to counter-rotate.

4. The surgical tool of claim 3, wherein the compliant member is pretensioned during assembly to provide a torque at or below a pre-tension limit of the first and second drive cables.

5. The surgical tool of claim 1, wherein the first one-way bearing is secured to an adapter and the adapter is matable with the upper capstan such that rotation of the adapter correspondingly rotates the upper capstan.

6. The surgical tool of claim 5, wherein the adapter and the upper capstan each provide matable interlocking features.

7. The surgical tool of claim 5, wherein the adapter defines a cavity sized to receive the first one-way bearing.

8. The surgical tool of claim 1, wherein the first one-way bearing is secured to the upper capstan.

9. The surgical tool of claim 1, wherein the first and second one-way bearings are selected from the group consisting of a one-way clutch bearing, a sprag-style bearing, an anti-reverse bearing, a ratchet mechanism, and any combination thereof.

10. A method of operating a surgical tool, comprising:
positioning the surgical tool adjacent a patient for operation, the surgical tool including:
a drive housing having an elongate shaft extending therefrom and an end effector operatively coupled to a distal end of the elongate shaft;
a drive input and input shaft rotatably mounted to the drive housing;
a drive assembly mounted to the input shaft and including an upper capstan rotatably mounted to the input shaft with a first one-way bearing, and a lower capstan rotatably mounted to the input shaft with a second one-way bearing; and a first drive cable coupled to the upper capstan and extending to the end effector, and a second drive cable coupled to the lower capstan and extending to the end effector;

actuating the drive input to rotate the input shaft in a first angular direction and thereby driving the upper capstan in the first angular direction to pull the first drive cable in a first linear direction;

rotationally disengaging the lower capstan from the input shaft when the input shaft rotates in the first angular direction;

actuating the drive input to rotate the input shaft in a second angular direction opposite the first angular direction and thereby driving the lower capstan in the second angular direction to pull the second drive cable in the first linear direction; and rotationally disengaging the upper capstan from the input shaft when the input shaft rotates in the second angular direction.

11. The method of claim 10, further comprising:

allowing the second drive cable to unwind from the lower capstan and move in a second linear direction opposite the first linear direction when the input shaft is rotated in the first angular direction; and allowing the first drive cable to unwind from the upper capstan and move in the second linear direction when the input shaft is rotated in the second angular direction.

12. The method of claim 11, further comprising wrapping a first length of the first drive cable onto the upper capstan when the input shaft rotates in the first angular direction and simultaneously unwrapping a second length of the second drive cable from the lower capstan, wherein the first and second lengths are the same.

13. The method claim 10, further comprising providing constant opposing torsional loads on the upper and lower capstans with a compliant member operatively coupled to and extending between the upper and lower capstans.

14. The method of claim 13, further comprising urging the upper and lower capstans to counter-rotate with the compliant member.

15. The method of claim 13, further comprising pretensioning the compliant member during assembly and thereby providing a torque at or below a pre-tension limit of the first and second drive cables.

16. The method of claim 13, wherein driving the upper capstan in the first angular direction further comprises removing slack in the second drive cable with the compliant member acting on the lower capstan, and wherein driving the lower capstan in the second angular direction further comprises removing slack in the first drive cable with the compliant member acting on the upper capstan.

17. A drive assembly for a surgical tool, comprising:

a first capstan assembly including an upper capstan rotatably mountable to an input shaft of the surgical tool with a first one-way bearing;

a lower capstan assembly including a lower capstan rotatably mountable to the input shaft with a second one-way bearing;

a compliant member operatively coupled to and extending between the upper and lower capstan assemblies, wherein the compliant member provides constant opposing torsional loads on the upper and lower capstan assemblies that urge the upper and lower capstans to counter-rotate; and a first drive cable securable to the upper capstan and extendable to an end effector of the surgical tool, and a second drive cable securable to the lower capstan and extendable to the end effector, wherein rotating the input shaft in a first angular direction rotationally disengages the lower capstan from the input shaft and drives the upper capstan in the first angular direction to pull the first drive cable in a first linear direction, and wherein rotating the input shaft in a second angular direction opposite the first angular direction rotationally disengages the upper capstan from the input shaft and drives the lower capstan in the second angular direction to pull the second drive cable in the first linear direction.

18. The drive assembly of claim 17, wherein rotating the input shaft in the first angular direction allows the second drive cable to unwind from the lower capstan and move in a second linear direction opposite the first linear direction, and wherein rotating the input shaft in the second angular direction allows the first drive cable to unwind from the upper capstan and move in the second linear direction.

19. The surgical tool of claim 17, wherein the first capstan assembly further includes an adapter matable with the upper capstan such that rotation of the adapter correspondingly rotates the upper capstan, and wherein the first one-way bearing is secured to the adapter.

20. The drive assembly of claim 17, wherein the first and second one-way bearings are selected from the group consisting of a one-way clutch bearing, a sprag-style bearing, an anti-reverse bearing, a ratchet mechanism, and any combination thereof.

* * * * *